US 6,602,293 B1

(12) United States Patent
Biermann et al.

(10) Patent No.: US 6,602,293 B1
(45) Date of Patent: Aug. 5, 2003

(54) POLYMERIC COMPOSITE ORTHOPEDIC IMPLANT

(75) Inventors: Paul J. Biermann, Columbia, MD (US); Jack C. Roberts, Columbia, MD (US); Amy A. Corvelli, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 1058 days.

(21) Appl. No.: 08/742,733

(22) Filed: Nov. 1, 1996

(51) Int. Cl.⁷ .................................................. A61F 2/28
(52) U.S. Cl. ................. 623/23.5; 623/23.51; 623/23.44; 623/23.58; 606/72
(58) Field of Search .................... 606/72; 623/FOR 16, 623/20 US, 23 US, 20.15–20.16, 22.41–22.46, 23.18, 23.44, 23.5, 23.51, 23.58

(56) References Cited

U.S. PATENT DOCUMENTS

| | | | |
|---|---|---|---|
| 4,038,703 A | * | 8/1977 | Bokros ........................... 623/2 |
| 4,190,044 A | | 2/1980 | Wood |
| 4,262,665 A | | 4/1981 | Roalstad et al. |
| 4,355,429 A | * | 10/1982 | Mittelmeier et al. .......... 623/20 |
| 4,375,810 A | | 3/1983 | Belykh et al. |
| 4,479,271 A | | 10/1984 | Bolesky et al. |
| 4,516,569 A | | 5/1985 | Evans et al. |
| 4,578,384 A | | 3/1986 | Hollinger |
| 4,634,445 A | | 1/1987 | Helal |
| 4,688,561 A | | 8/1987 | Reese |
| 4,750,905 A | | 6/1988 | Koeneman et al. |
| 4,781,181 A | | 11/1988 | Tanguy |
| 4,790,302 A | | 12/1988 | Colwill et al. |
| 4,808,186 A | | 2/1989 | Smith |
| 4,813,960 A | | 3/1989 | Muller |
| 4,827,919 A | | 5/1989 | Barbarito et al. |
| 4,834,747 A | | 5/1989 | Gogolewski |
| 4,834,756 A | | 5/1989 | Kenna |
| 4,863,475 A | | 9/1989 | Andersen et al. |
| 4,877,019 A | | 10/1989 | Vives |
| 4,898,186 A | | 2/1990 | Ikada et al. |
| 4,946,459 A | | 8/1990 | Bradhshaw et al. |
| 4,955,911 A | | 9/1990 | Frey et al. |
| 4,978,355 A | | 12/1990 | Frey et al. |
| 5,009,664 A | | 4/1991 | Sievers |
| 5,032,129 A | * | 7/1991 | Kurze et al. ................... 623/16 |
| 5,053,035 A | | 10/1991 | McLaren |
| 5,098,433 A | | 3/1992 | Freedland |
| 5,108,398 A | | 4/1992 | McQueen et al. |
| 5,122,141 A | | 6/1992 | Simpson et al. |

(List continued on next page.)

FOREIGN PATENT DOCUMENTS

| | | | | |
|---|---|---|---|---|
| GB | 2216425 | | 10/1989 | |
| SU | 1667854 A1 | * | 8/1991 | ................... 623/16 |
| SU | 1718876 A1 | * | 3/1992 | ................... 606/72 |

OTHER PUBLICATIONS

Helen Worth, APL News, Dec. 1995, p. 1 and 5, vol. 51, No. 12; Laurel, Maryland.The Johns Hopkins University—Applied Physics Laboratory.

Primary Examiner—David H. Willse
(74) Attorney, Agent, or Firm—Francis A. Cooch

(57) ABSTRACT

An orthopedic implant comprising a thermoplastic polymer or a composite comprising, in one embodiment, polyetheretherketone reinforced with 10% by volume of glass fibers, with an elastic modulus approximating the elastic modulus of bone. A porous coating is formed on the implant surface by creating a roughness thereon, by coating the surface with hydroxyapatite or by embedding a biocompatible material such as titanium in the surface. A two piece embodiment of the implant is joined and locked together, after the opposite ends of each piece are inserted in the medullary canal, using an interlocking mechanism comprising a fluted protrusion on one piece and a corresponding fluted cavity in the other piece with the fluted portions being complementarily tapered.

24 Claims, 8 Drawing Sheets

U.S. PATENT DOCUMENTS

| | | |
|---|---|---|
| 5,171,284 A | 12/1992 | Branemark |
| 5,181,930 A * | 1/1993 | Dumbleton et al. ........... 623/23 |
| 5,236,457 A | 8/1993 | Devanathan |
| 5,244,623 A | 9/1993 | King |
| 5,248,313 A | 9/1993 | Greene et al. |
| 5,250,049 A * | 10/1993 | Michael ....................... 606/72 |
| 5,281,226 A | 1/1994 | Davydov et al. |
| 5,334,184 A | 8/1994 | Bimman |
| 5,360,448 A * | 11/1994 | Thramann .................... 623/16 |
| 5,417,692 A * | 5/1995 | Goble et al. .................. 606/73 |
| 5,443,513 A * | 8/1995 | Moumene et al. ............ 623/16 |
| 5,554,192 A | 9/1996 | Crowninshield |
| 5,653,764 A * | 8/1997 | Murphy ....................... 623/23 |

* cited by examiner

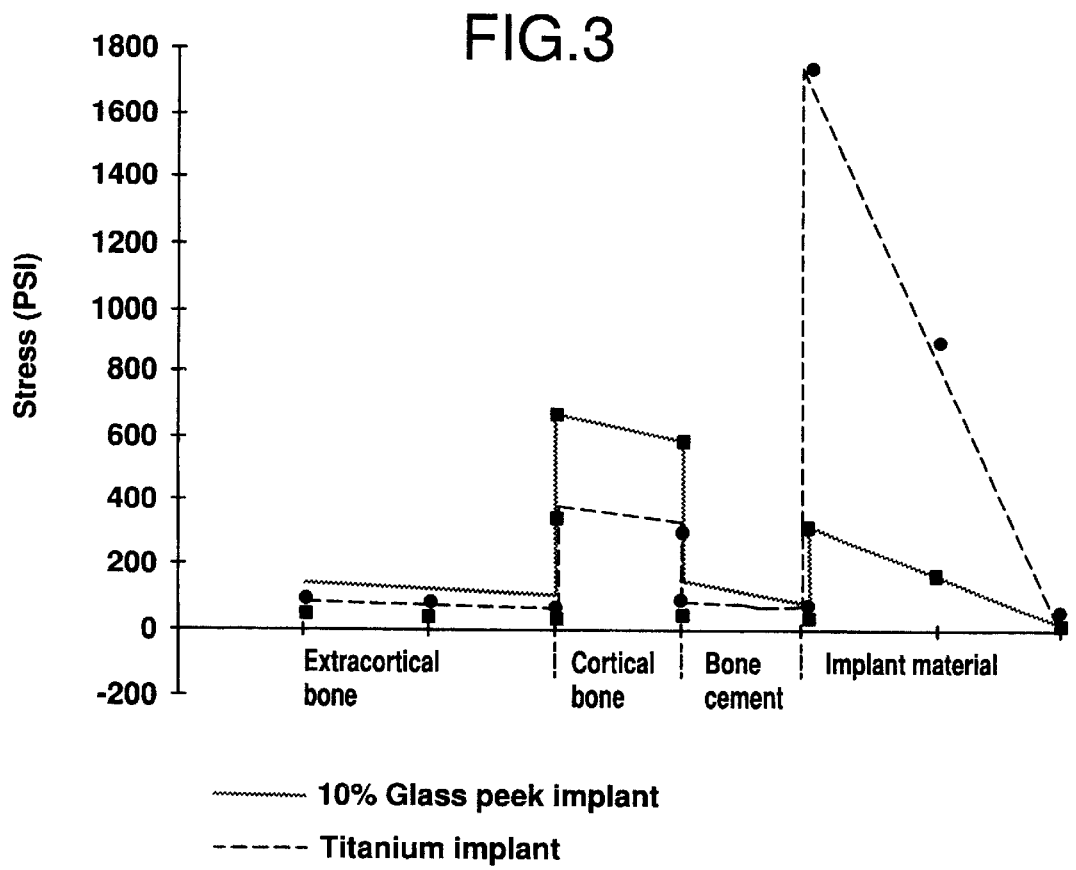
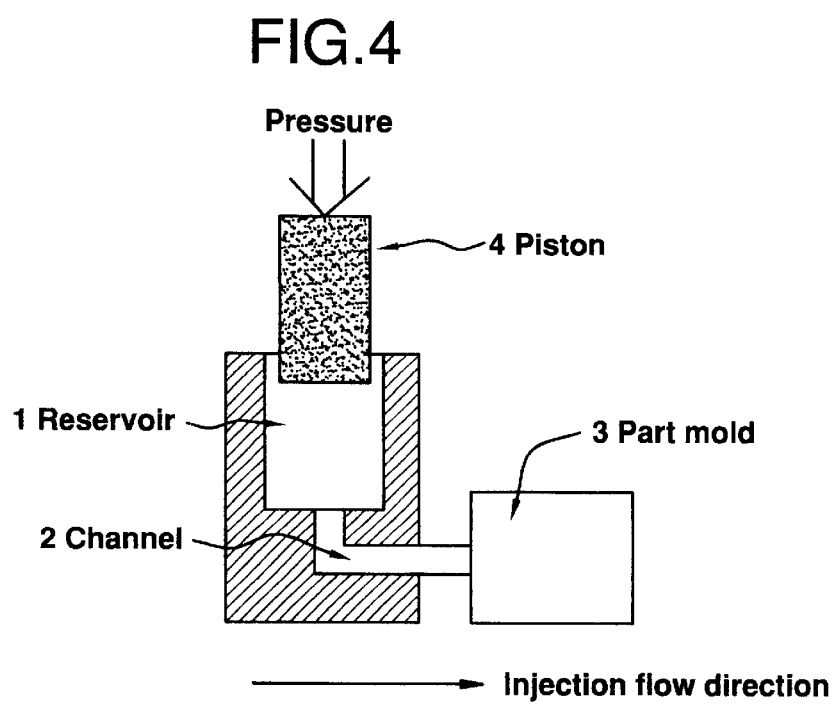

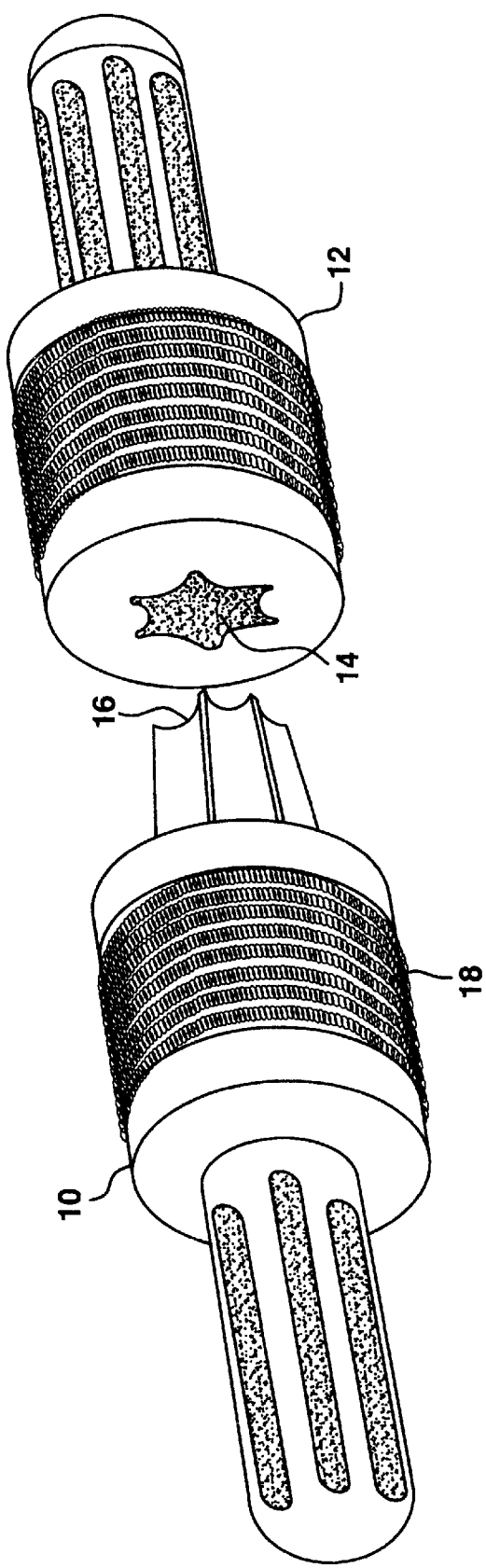

POLYMERIC COMPOSITE ORTHOPEDIC IMPLANT

STATEMENT OF GOVERNMENTAL INTEREST

This invention was made with Government support under Contract No. N00039-95-C-0001 awarded by the Department of the Navy. The Government has certain rights in the invention.

BACKGROUND OF THE INVENTION

The invention relates to orthopedic (bone) implants which are used to replace a missing or diseased portion of bone. Several conditions can lead to the loss of bone including trauma, arthritic diseases, tumors, musculoskeletal defects, and the replacement of a failed implant.

An intramedullary implant is generally used in long bones (i.e., the femur and humerus), and is inserted into the medullary canal, which runs through, the diaphysis (shaft) of the bone and is filled with bone marrow. A long bone implant is one of two different types of intramedullary implants, the other being categorized as joint replacements. The joint replacement implants (i.e., a hip or knee implant) have a much more complicated geometry, than the rod-like, long bone replacement. Both types of implants have shown similar modes of failure in clinical studies.

The intramedullary implants being used today are generally fabricated from metal, using an alloy of either titanium (Ti) or cobalt chrome (Co-Cr). The joint replacement implants are primarily made with a Co-Cr alloy containing molybdenum (Mo), which is added to improve the wear resistance properties of the material, an important consideration when the implant is used to replace articulating surfaces.

Long bone replacement implants are most commonly fabricated from Ti, either in its commercially pure state or as an alloy with aluminum and vanadium. These materials have been experimentally and clinically proven to be biocompatible. It is not completely understood biochemically, but the bone tissue grows and attaches to the surface of Ti more readily than to other materials. This property allows Ti to aid in the fixation of the implant in bone, an extremely important part of the operation directly affecting the duration of success.

It is important for implant success that the implant remain stationary so the bone tissue can begin to grow around it. Initial stabilization is achieved through the use of bone cement applied during surgery, which acts as a filler between the bone and the implant. The interfacial space is filled with cement to stabilize the implant and inhibit motion. The bone cement material is a thermoset particulate composite polymer called polymethylmethacrylate (PMMA).

Long term stabilization of the implant in bone is achieved by having a porous coating on the surface of the implant. The porous coating is either added or molded onto the surface of the implant. Ti or hydroxyapatite (HA) are two materials with good biocompatibility and/or biostimulating factors commonly used to create this porous coating. Ti is sintered onto the metal (e.g., Ti) implant in either a mesh of crimped wire or a random array of particulates. The HA is applied to the surface of the implant using plasma spraying techniques.

The surface coating must have large enough pores to allow the bone cells to travel through and create a strong interlocking fixation by reconnecting with adjacent bone tissue throughout the mesh. This method of fixation relies on the connection of the bone tissue to hold the implant in place. If the bone tissue does not grow fast or is not strong enough, the implant is not completely stabilized and micromotion can occur.

Problems with current implant designs stem from the difference in mechanical properties between the materials used in the implant system and the bone itself. The Ti alloy has an elastic modulus equal to 110.3 GPa ($16.0 \times 10^6$ psi), and the Co—Cr alloy has an elastic modulus equal to 210.3 GPa ($30.5 \times 10^6$ psi). In comparison to the modulus of cortical bone, equal to about 13.8 GPa ($2.0 \times 10^6$ psi), these metallic implants are a minimum of eight times stiffer. This large gradient causes stress shielding across the implant-bone interface, where the implant supports and absorbs most of the load and leaves the bone virtually inactive and unstressed.

As stated in Wolff's law, bone needs to be cyclically stressed to survive and remain strong enough to support the body. The shielded, unstressed bone around a metal implant begins to resorb and cavities form between the implant and the bone. The cavities weaken the fixation and allow micromotion of the implant in the bone, eventually producing local wear debris. Microscopic foreign body wear debris in the surrounding tissue will trigger the body's defense mechanism and cause infectious reactions. Loosening of the implant is irreversible without intervention and ultimately leads to a revision operation. A patient can only undergo two or three additional procedures before the bone becomes too weak and osteoporotic to support another replacement and is considered non-functional.

SUMMARY OF THE INVENTION

The isoelastic bone-implant system of the invention minimizes, if not eliminates, the stress shielding effect created by a metal implant, thus, leading to a longer implant lifetime in the body. In one embodiment, a thermoplastic polymer with an elastic modulus approximating the modulus of bone is used for the implant.

Since bone is a natural composite material composed of a matrix with organic and inorganic substances, composites are also an excellent choice of materials to use for implants, specifically for those situations where material properties have a large impact on the implant's success, such as replacement of a hip. Hence, a second embodiment comprises a composite comprising a thermoplastic polymer and a reinforcing material, the composite having an elastic modulus approximating the elastic modulus of bone. The composite preferably comprises polyetheretherketone (PEEK), a high temperature thermoplastic, containing preferably 10% by volume of chopped E-glass fibers which results in a material having approximately the same stiffness as bone and, therefore, in a significant improvement with respect to the stress-shielding problem.

The final step is the application or formation of a porous coating on the surface of the implant to create the porous environment for bone ingrowth. The coating can comprise hydroxy-apatite applied to the surface, a roughness formed on the surface, or a biocompatible material such as titanium embedded in the surface.

A two piece embodiment of an intramedullary implant is joined and locked together, after the opposite ends of each piece are inserted in the medullary canal, using an interlocking mechanism comprising a fluted protrusion on one piece and a corresponding fluted cavity in the other piece with the fluted portions being complementarily tapered.

BRIEF DESCRIPTION OF THE DRAWINGS

FIG. 3 is a plot of the stress gradients through the different material layers for the metallic and composite implants produced from the FEM.

FIG. 4 is a schematic representation of the in-house injection molding assembly.

FIG. 7 illustrates the implant of the invention with the mating flutes and the tip flutes.

DETAILED DESCRIPTION OF THE INVENTION

The first step in producing the implant of the invention was to develop a material that has similar bulk mechanical properties to those of bone. A number of polymers have such properties including some polymers that may be stiff enough to use as an implant without the need for reinforcing fibers, e.g., Poly-X™ Self-Reinforced Polymers manufactured by Maxdem Inc. of San Dimas, Calif. A key aspect of the invention is the use of a material as an implant that has an elastic modulus approximating the elastic modulus of bone.

For a composite implant, a high temperature thermoplastic polymer, polyetheretherketone (PEEK), was chosen as the resin, or matrix, material for its relatively comparable strength, high toughness and previously recorded biocompatibility with human tissue cells. E-glass fibers were selected as the reinforcing material for their strength.

Although carbon fibers can be used in PEEK, glass fibers were chosen because the material was more cost effective, and the injection molding of the preforms (described below) was easier because the glass fibers are less abrasive than carbon. Most importantly, the glass fibers are transparent to radiation therapy and will not create shadows or interfere with post-operative treatment. Properties of these constituent materials are listed in Table 1.

TABLE 1

ELASTIC MODULI FOR THE RESIN AND FIBER MATERIALS OF THE COMPOSITE

| Material | Elastic Modulus GPa (psi) | Poisson's Ratio |
| --- | --- | --- |
| PEEK resin | 4.2(0.6 × 10⁶) | 0.41 |
| E-glass fibers | 72.4(1.1 × 10⁷) | 0.20 |

To predict the properties of PEEK with glass fibers, a software package, called SMC Micromechanics Model for Composite Materials, developed to determine thermoelastic properties of fiber reinforced composite materials, was used. This program uses the constituent properties of the resin and reinforcement phases, their composition, the fiber aspect ratio, and degree of orientation of the reinforcement throughout the resin, to calculate a longitudinal modulus for the composite material. The longitudinal modulus for the implant substrate being created was chosen to be slightly lower than that of bone in anticipation of the additional stiffness and strengthening of the biocompatible, metallic porous surface to be added later on in the fabrication process.

Commercial compounding services typically provide fiber volumes of 10%, 20% and 30% for both glass and graphite fibers. These are the compositions used in the SMC program to determine material properties. Instead of relying solely on commercial data published for these materials, the program was used to predict the properties of the same compositions but with varying fiber orientations.

Figure 1:
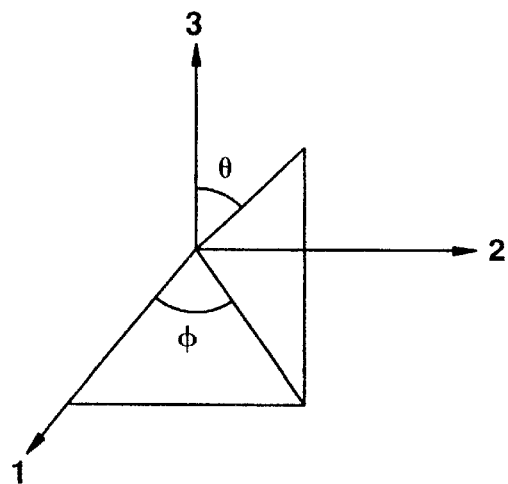
FIG. 1 illustrates the orientation parameters in the SMC Micromechanics Model for Composite Materials software program.

Two parameters are used to describe the fiber orientations. The parameter $f_p$ describes the planar fiber orientation in the 1-2 plane, and $f_a$ defines the axial orientation relative to the 3 axis (FIG. 1). The program was run to find the range of moduli for each composition from a completely random distribution of fibers to a relatively aligned distribution. The values are listed in Table 2.

TABLE 2

OUTPUT FROM SMC PROGRAM FOR PEEK COMPOSITES

| Composition (% fiber) | Longitudinal Modulus GPa (psi) | |
| --- | --- | --- |
| | Completely Random | Perfectly Aligned |
| 10% E-glass | 6.05 (0.88 × 10⁶) | 10.54 (1.53 × 10⁶) |
| 20% E-glass | 8.22 (1.19 × 10⁶) | 16.98 (2.46 × 10⁶) |
| 30% E-glass | 10.65 (1.55 × 10⁶) | 23.15 (3.36 × 10⁶) |
| 10% graphite | 6.89 (0.99 × 10⁶) | 16.27 (2.36 × 10⁶) |

A composition of PEEK with 10% glass fibers had a predicted modulus range from 6.05 GPa.(0.88×10⁶ psi) to 10.54 GPa (1.53×10⁶ psi) for completely random to completely aligned fiber orientations respectively. Note that both values are still less than the modulus of bone of 13.79 GPa (2×10⁶ psi). The lowest volume ratio (10%) of graphite fibers available predicted a range of moduli with an upper limit that was already greater than the modulus of bone. Therefore, the composition of PEEK with 10% glass fibers was chosen to be the substrate material for the composite implant.

Figure 2:
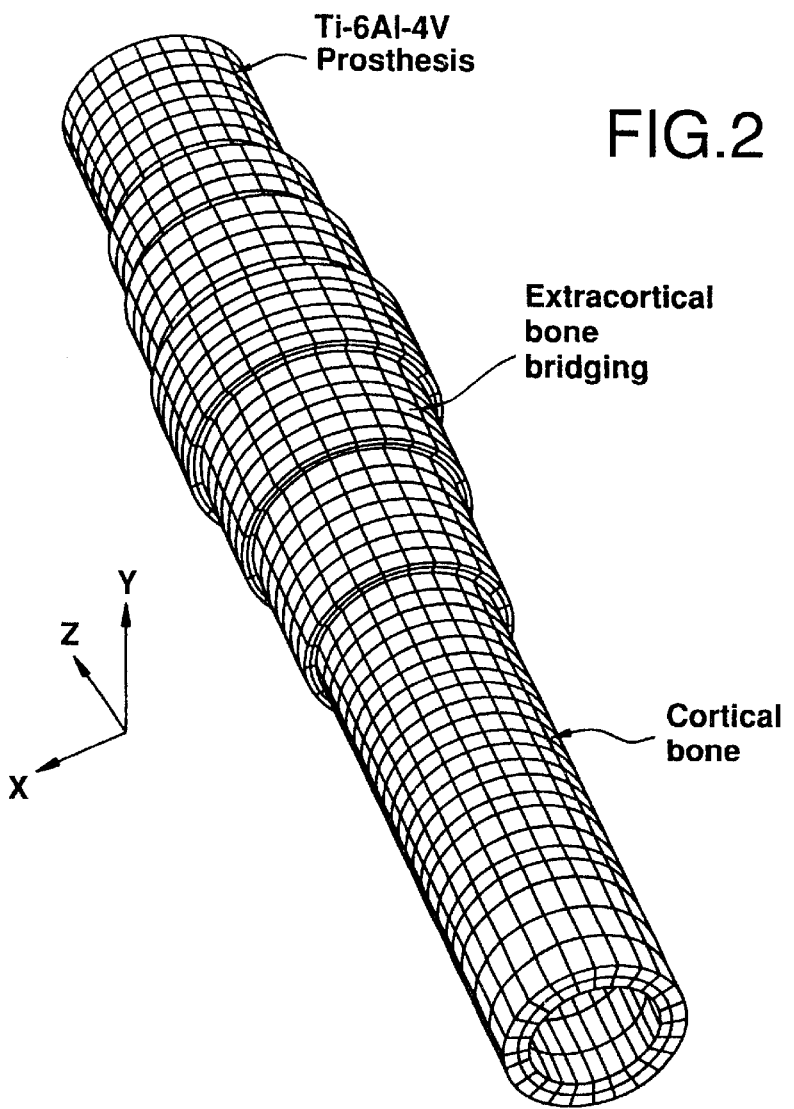
FIG. 2 illustrates a three-dimensional finite element model (FEM) of a prosthesis with bone cement, and cortical bone with extracortical bone bridging.

The properties determined by SMC were then used in the development of a finite element model (FEM), created using COSMOS/M Finite Element Analysis Software. The model was made to study the induced stresses surrounding a bone replacement in vivo and compare the differences between a metallic and a composite implant. The model contains an implant, bone cement, cortical bone, and extracortical bone layer in a three-dimensional array shown in FIG. 2. The stresses resulting from an applied bending moment were studied, since they had more significance than the stresses resulting from axial and torsional loads. A comparison was made between the resultant stresses of a Ti and 10% glass-PEEK implant.

The bending moment applied to the FEM produced longitudinal stresses through the implant and the bone, the most critical stress case in consideration of stress shielding. The magnitudes of the stresses, in a section where the extracortical bone bridging is the thickest, were plotted in FIG. 3. The gradients of these stresses radially outward, through the extracortical bone, cortical bone, bone cement, and implant layers, are evident in the graph.

While the stress that the composite implant bears is much lower than that for the metallic implant, the stress in the cement and bone layers are higher for the composite implant than for the Ti. This is a direct result of matching the elastic modulus of the composite to that of bone. The composite implant is not bearing as much load as the metallic implant, allowing the bone to absorb more of the applied load. Therefore, the cortical bone layer bears more load when using the composite implant, theoretically confirming that an implant with properties closer to that of bone leads to the elimination of the stress shielding effect evident with higher modulus metallic implants.

Prototypes of the composite implant were made using a pressure/injection molding system, shown in FIG. 4, developed specifically for this project. The assembly consists of a reservoir (1), where the material sits and heats up to its molten state, with a channel (2) that is opened and closed by a two-way valve connecting the reservoir to the mold (3), which is tightly clamped together. The injection speed was controlled by pressure applied via a piston (4) to the material in the reservoir. The material was released when the valve was opened and pushed into the end of the mold in the direction of the long axis of the part. Temperatures of the reservoir and the mold were controlled individually by a set of four heaters each.

To condition the system initially, lower temperature thermoplastic materials were used. This allowed trial observations of the process and the discovery of any necessary modifications to be made, prior to injecting the high temperature PEEK. Molding parts using ultra high molecular weight polyethylene, acrylic, polycarbonate, and glass fiber filled polycarbonate progressively seasoned the tool to the higher temperatures. The modifications made were done to improve the density of the parts being produced, including the addition of bleed holes in the mold to allow the escape of air pockets and the adjustments of the injection and back pressures held on the part. Through this trial period, it was discovered that a high pressure at the opening of the valve followed by a lower pressure during cooling of the part increased their density.

Small pellets of 10% glass-filled PEEK, were heated up to 680° F. to reach its molten state. Since PEEK is such a highly viscous material even in its molten form, the injection pressure was set at 75,000 psi. A 30,000 psi back pressure was held while the part cooled from 450° F. to 275° F. The high initial pressure created the fastest injection speed within the constraints of the system, and the back pressure forced residual air pockets to escape. The production rate was fairly slow due to the lag time in heating and cooling the system each day, the limited amount of material used from one filling of the reservoir, and the manual assembling and disassembling of the mold to make each individual part.

The prototype molded part is a preform of the final implant. Several additional machining and molding processes have to be performed to reach the final shape. Testing was done to prove that the material properties of the molded parts were consistent with those of commercially provided material samples. Scanning was performed to make a visual assessment of the part density. A cross-section was photographed under magnification to measure the fiber distribution throughout the body of the part.

Unlike a high production commercial extruder/injection line, the material processed in the above assembly remained molten for a much longer time, resulting in some oxidation. Characterization testing was performed to confirm that the parts being produced had retained the original material properties. Tensile tests were run on a group of six randomly selected molded preforms machined to fit an extensometer and have a one inch gage length.

The tensile test results were compared with those from tensile tests done on commercially supplied tensile bars of different compositions of glass-filled PEEK. The commercial tensile bars were run to failure and ultimate tensile strengths were measured. The "in-house" samples failed in the threads used to fit the machine and the ultimate tensile strengths were never reached. The elastic moduli, listed in Table 3, were comparable for all tests, confirming the predictions of the SMC program and verifying that the material integrity was conserved through the in-house molding process.

TABLE 3

TESTING RESULTS CONFIRMING
ORIGINAL MATERIAL PROPERTIES

| Material | Elastic Modulus GPa (psi) | Tensile Strength MPa (Psi) |
|---|---|---|
| bone (femur) | 17.2 (2.49 × 10$^6$) | 121.0 (17,500) |
| neat PEEK (0% glass) | 3.66 × 0.13 (0.53 ± 0.02 × 10$^6$) | 92.7 ± 1.05 (13,450 ± 151.7) |
| molded 10% glass/PEEK* | 7.86 ± 2.17 (1.14 ± 0.32 × 10$^6$) | 81.1 ± 13.56** (11,765 ± 1966.6)** |
| commercial 10% glass/PEEK | 6.62 ± 1.99 (0.96 ± 0.29 × 10$^6$) | 110.72 ± 8.71 (16,060 ± 1262.7) |
| commercial 20% glass/PEEK*** | 8.96 ± 0.49 (1.30 ± 0.07 × 10$^6$) | 149.33 ± 2.47 (21,660 ± 357.8) |
| commercial 30% glass/PEEK*** | 1.10 ± 0.79 (1.60 ± 0.12 × 10$^6$) | 164.62 ± 1.42 (23,877.5 ± 206.6) |

*in-house molded preforms
**tensile strength measured when failed at threads
***commercially provided ASTM standard tensile test bars The PEEK/10% glass composite preforms were also evaluated non-destructively via C-scanning to observe if there were voids or air pockets in the parts that might eventually interfere with the strength of the part. The scans were calibrated to a sectioned part to see what signals corresponded to impurities and discontinuities in the material. The rest of the parts were non-destructively scanned, and the results showed consistently solid parts with no significant defects.

Figure 5:
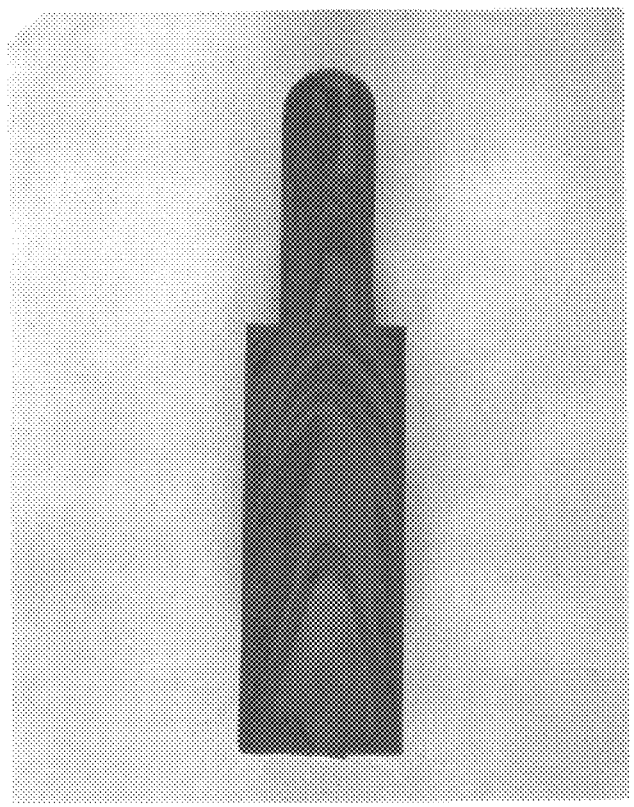
FIG. 5 is a photograph of a randomly selected, longitudinally sectioned PEEK/10% glass preform.

A random preform part was chosen and cross-sectioned, exposing the flow pattern of the injected composite material (see FIG. 5). Images of the micro-polished cross section were captured at 40× magnification using an optical microscope, producing a clear picture of the fibers. The image was then digitally imported into NIH Image software to measure the fiber off-axis angles with respect to the horizontal (longitudinal axis). Fiber-angles were measured from images taken along the center-line of the part in a two-dimensional plane, spaced approximately 0.1375 inches apart. The angle measured from these images represents the position of the fiber in the 1-2 plane as described with the SMC program (see FIG. 1).

Figure 6A:
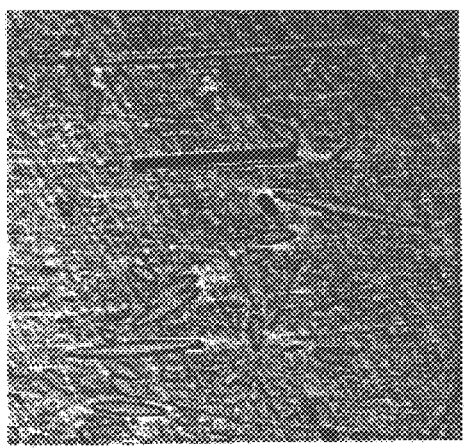
FIG. 6, consisting of FIGS. 6a and 6b, are, respectively, an image showing relatively aligned fibers (darkened) lying predominantly in the 1-2 plane; and an example of fibers pointed into the plane, and thus not chosen for measurement of orientation.
Figure 6B:
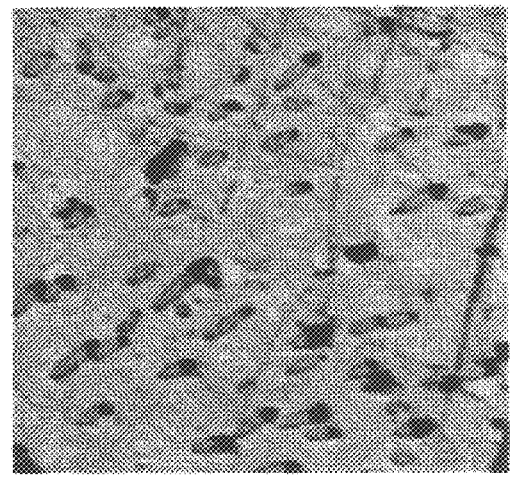

Only the fibers that were predominantly laying in that plane were selected to be measured (FIG. 6a). The average off-axis angle was 26.13 degrees with the range spanning from 0 degrees to 93.92 degrees. Assuming that the same results would be seen in the plane going into the screen (FIG. 6b), these images confirm that the fiber orientation may be classified as completely random. The values taken from the SMC data are further verified to be accurate with the modulus predicted and the orientation assumed with input.

As shown in FIG. 7, an implant of the invention comprises first and second pieces 10, 12, each with a tip or end that fits into the intramedullary canal and extends from a wider body that has the porous coating to support the growth of extracortical bone. Each tip is inserted into the medullary cavity of either end of the fractured bone at the diseased or damaged site deep enough to assure anchorage into healthy bone. The second piece has a cavity 14 for receiving a protruding member 16 on the first piece. The two pieces which are complementarily tapered for ease of alignment and assembly are joined by being tapped together and locked by the tapered press fit.

The intramedullary implant is also designed with a means for resisting rotation between the first and second pieces. In one embodiment this comprises a six-fluted interlock to insure that the implant is rotationally stable. Flutes were chosen to minimize stress concentration while maximizing interlock or fixation but any keyed or indexed means to prevent rotation, such as notches and recesses, are acceptable. In addition to using an adhesive to seal this connection, the mating flutes apply a positive lock during torsion.

The design of a six-fluted mating interlock is alterable in consideration of the surgical procedure for implanting these devices. The addition of more flutes would retain the strength and resistance to torsional forces, while decreasing the angle between each mating flute. This decrease in angle would make it much easier to match the two halves when securing them together during surgery, where time may be a major concern.

The interlocking flutes are molded onto/into the ends of the preforms, and are designed to have a friction lock when tapped together, making the sizing and accuracy of the molding very critical. The flutes on the tips (the ends that are inserted into the medullary cavity of bone) provide more surface area for the bone cement to fill and hold the implant in place.

The final step in making the implant is to embed a tight Ti coil 18 (FIG. 7) into the surface of the body of the implant by, for example, wrapping the coil around the implant and pressing the coil into the polymer after or during an application of heat. Titanium is used for its biocompatibility. The critical design aspect of this surface, aside from achieving a strong attachment of the Ti to the composite, is its porosity. In order to allow the necessary bone cells to fit through the pores and create the desired mechanical interlock, the pores, i.e., the interstices between the exposed (nonembedded) portions of the Ti wire coil, should be in the range of 150–200 $\mu$m which may require that the wire coil be inter-meshed, i.e., overlapped, to achieve.

The desired porosity may also be achieved by using HA on the implant surface instead of Ti or, without Ti or HA, by forming different surface roughnesses on the material forming the implant. Surface roughness on any material increases bone cell attachment and can be created by using a mold with a roughen surface or by some treatment, e.g., etching, sanding or sandblasting, of the implant after the molding process.

The titanium coil can be embedded into the polymer via one of several methods, all of which should be done in a vacuum or inert gas atmosphere: 1) the coil is heated via electrical resistance while being pressed into the polymer; 2) the coil is preheated in an oven and then placed around the polymer while being pressed into place; 3) the coil is heated by induction in a high frequency RF field while being pressed into the polymeric surface; 4) the coil and polymer surface are both heated by a focused hot gas stream while the coil is pressed into the polymer; and 5) the coil and the polymer are both heated at the intersection point by a focused infrared beam while the coil is wrapped around the polymeric implant and imbedded. In each case the coil should only be embedded in polymer ⅓ to ½ of its diameter when the process is completed. Also, the mechanism for imbedding the coil should not interfere with the heating method.

Figure 8A:
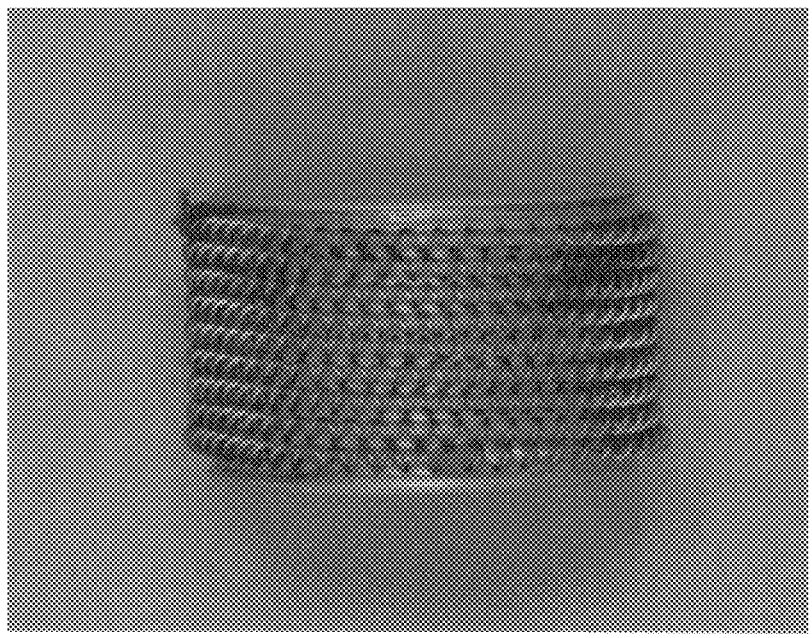
FIG. 8, consisting of FIGS. 8a and 8b, shows, respectively, the winding of the Ti coil around [a section of] the implant; and a magnified picture of the embedded Ti in the surface of the PEEK.
Figure 8B:
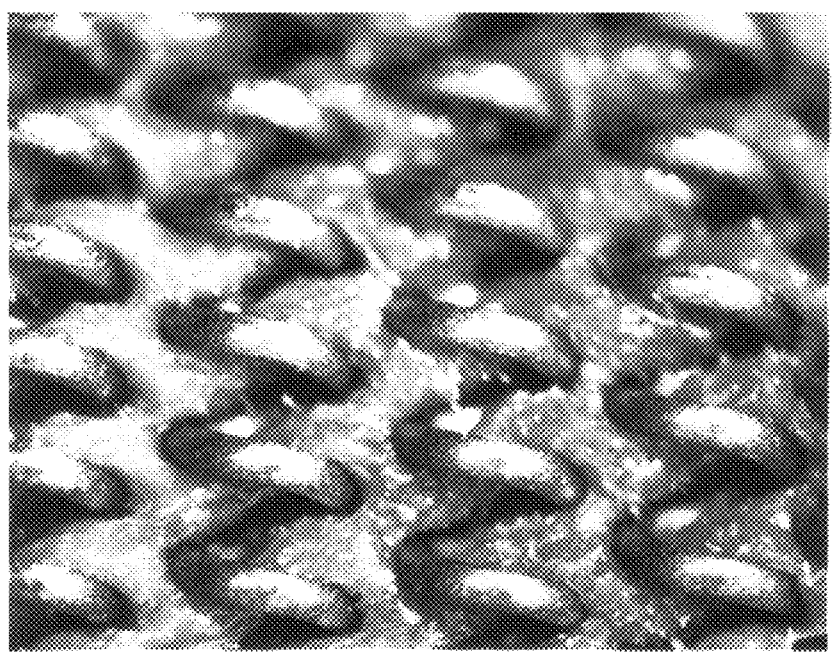

The result is a process that leaves the Ti coil embedded into the surface of the PEEK approximately halfway, as shown in the photographs in FIG. 8. Push out tests were performed to prove the Ti coil was securely embedded and mechanically locked into the surface of the PEEK implant. For each test, a section of the implant was set in an epoxy, using a 33:100 ratio of EPON Curing Agent V-40 to EPON Resin 826. The epoxy represented bone tissue surrounding the implant, creating a mechanical interlock through and around the Ti coil. The tests were done on an Instron Machine performing general compression of a cylinder.

Figure 9:
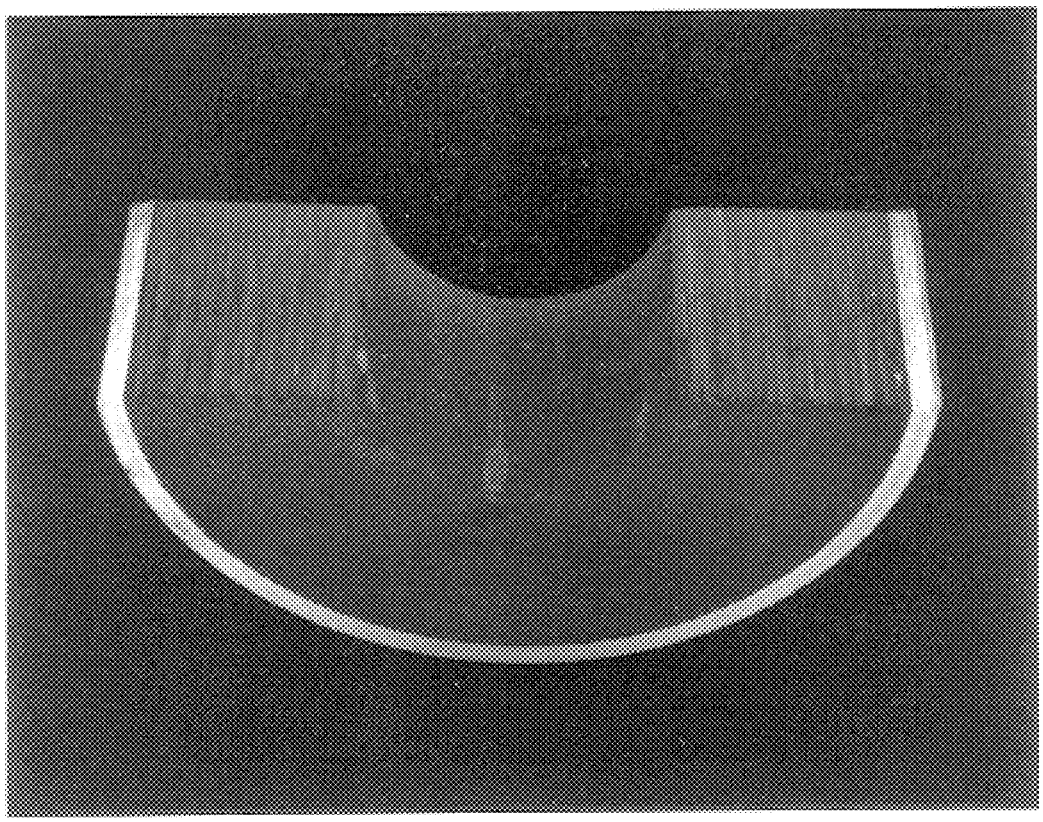
FIG. 9 illustrates a push-out test cross-section of epoxy (magnified 2x), representing bone tissue, that surrounded a PEEK implant that did not have a Ti wire coil embedded in the implant surface.

In order to prove that the results of the push-out tests represent the forces at the interface of the coil and the epoxy, instead of the PEEK and the epoxy, an initial test was done using a section of the implant without any coil embedded in the surface. The results showed that there was no bonding of the epoxy to the PEEK. The implant was smoothly pushed out with a maximum load of 540 lb, creating a shear stress of 419 psi. FIG. 9 is a cross-sectional picture of the epoxy that surrounded the part. It is obvious that there was no shearing or failure of the epoxy, which would have resulted if it bonded with the PEEK.

Tests were then done using sections of the implant with the coil embedded in the surface. Three tests were done with a low rate of displacement, applied at a constant 0.05 in/min. The maximum recorded push out load was an average of 3386 lbs, with an average maximum shear stress of 2269 psi. Test 4 was done with a higher rate of displacement, applied at a constant 10 in/min. The maximum force approximately doubled compared to the slower tests.

Figure 10:
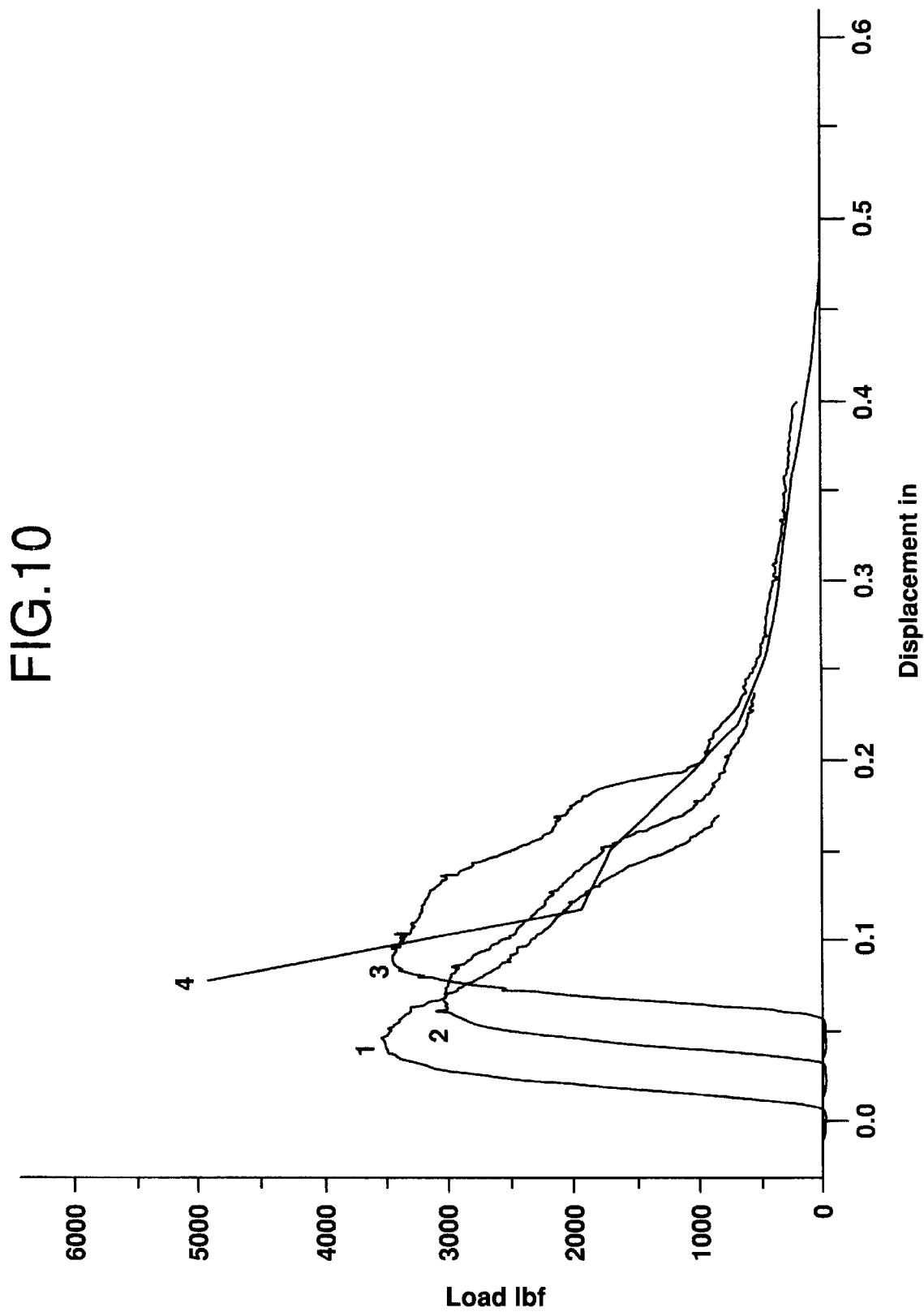
FIG. 10 is a plot of load v. displacement for four push-out tests for sections of epoxy, representing bone tissue, surrounding a PEEK implant having a Ti wire coil embedded in the implant surface.
Figure 11:
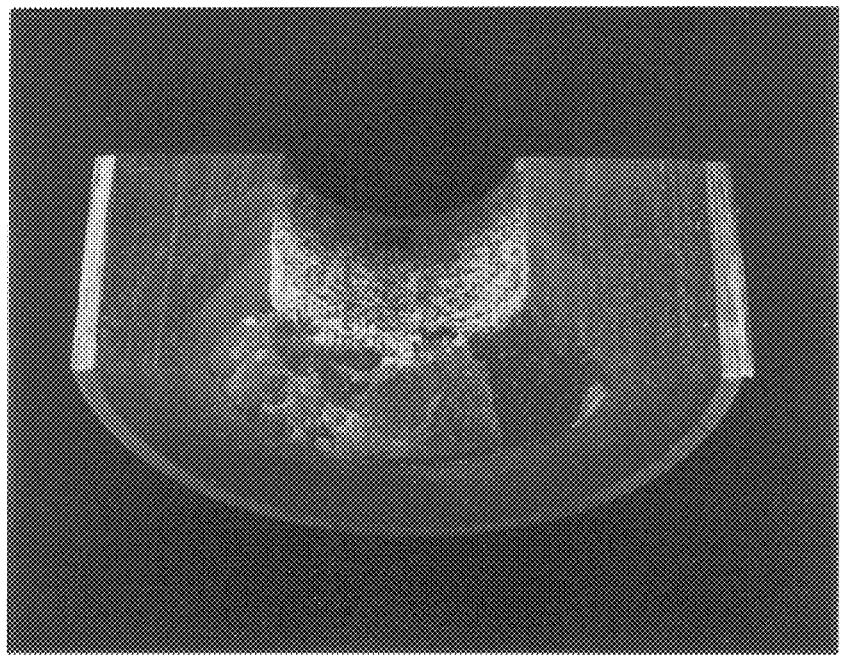
FIG. 11 illustrates a push-out cross-section of the epoxy (magnified 2x), representing bone tissue, that surrounded the PEEK implant with Ti wire coil embedded therein.
Figure 12:
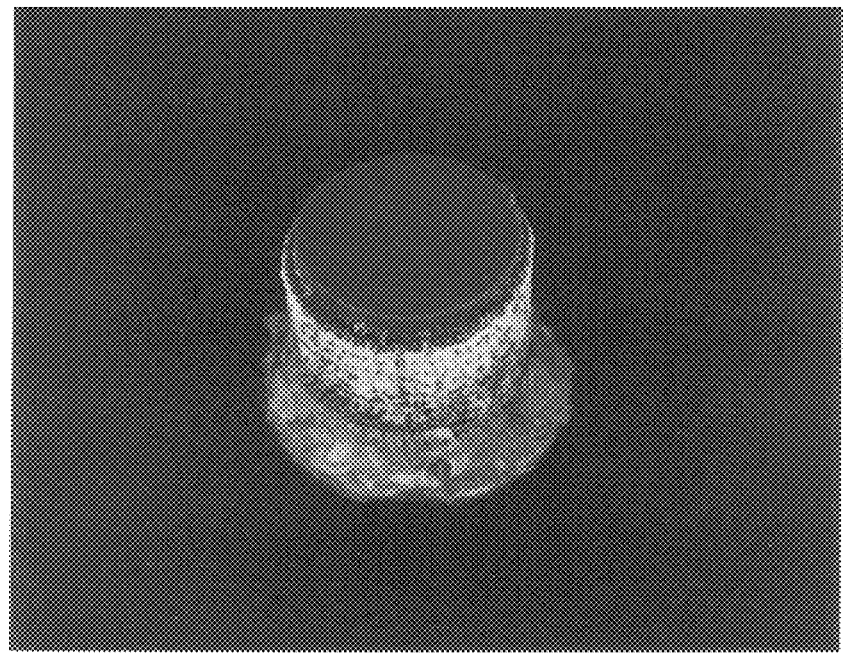
FIG. 12 illustrates the PEEK implant with embedded Ti wire coil (magnified 2x) after being pushed completely through the epoxy.

The load vs. displacement curves for all tests are shown in FIG. 10. The consistency is obvious with tests 1–3 and a steeper slope is shown for test 4 (this maximum force was not recorded quickly enough and was therefore estimated from the ultimate shear stress of the epoxy, since the epoxy completely failed). FIG. 11 is a cross-sectional picture of the epoxy that surrounded the part. The Ti sheared out of the epoxy and remained completely anchored in the PEEK, eventually fracturing the epoxy. The mechanical interlock of the epoxy in the coil pulled the epoxy with it as it was pushed through. FIG. 12 shows the part after being pushed completely through the epoxy. The amount of epoxy that remained attached to the coil proves that the mechanical interlock of the material through the porous surface is extremely strong.

The push out tests confirm that the Ti coil is mechanically locked in the surface of the implant. Considering that the most damaging strain the implant/coil interface would experience when implanted in vivo is in shear, these tests have proven that the Ti coil is essentially permanent in the surface. The amount of epoxy remaining in the coil as it was pushed through shows that this type of porous surface is more than adequate at providing enough space for a material (i.e., the epoxy in the test and bone tissue in vivo) to grow throughout it and create a mechanical interlock. Test 4 (performed with a higher rate of displacement) simulates a worst case scenario of the force the implant might see if the repaired bone experiences a major impact.

Clinically, the use of an implant that has an elastic modulus approximating the elastic modulus of bone will have a great impact on the orthopedic industry. Long term advantages of this new technology include a decline in the amount of revision surgeries necessary, reducing the rise of health care costs. The new implant will have a longer fatigue life, which will better serve the younger patient population, with a lower probability of recurring pain and surgery for the patient.

We claim:

1. An orthopedic implant for replacing a missing or diseased portion of bone, the implant comprising:
   a thermoplastic polymer having an elastic modulus approximating the elastic modulus of bone;
   a biocompatible material partially embedded in a surface of the implant;
   a first piece and a second piece, the first and second pieces being joined and locked together by an interlocking means comprising:
      a protruding member on the first piece; and
      a cavity in the second piece for receiving the protruding member; and
   means for resisting rotation between the first and second pieces, wherein the rotation resisting means comprises a flute on the protruding member and a corresponding fluted opening in the cavity.

2. An orthopedic implant for replacing a missing or diseased portion of bone, the implant comprising:
   a thermoplastic polymer having an elastic modulus approximating the elastic modulus of bone;
   a biocompatible material partially embedded in a surface of the implant;
   a first piece and a second piece, the first and second pieces being joined and locked together by an interlocking means comprising:
      a protruding member on the first piece; and
      a cavity in the second piece for receiving the protruding member,
      wherein the protruding member and the cavity are complementarily tapered; and
   means for resisting rotation between the first and second pieces.

3. The implant as recited in claim 2, wherein the end opposite the protruding member on the first piece and the end opposite the cavity on the second piece are both fluted.

4. An intramedullary implant for replacing a missing or diseased portion of bone comprising:
   a first piece comprising a first end for insertion into the medullary cavity of a bone and a second end having a protruding member thereon;
   a second piece comprising a first end for insertion into the medullary cavity of a bone and a second end having a cavity formed therein for receiving the protruding member on the second end of the first piece; and
   means for resisting rotation between the first and second pieces;
   wherein the rotation resisting means comprises a flute on the protruding member and a corresponding fluted opening in the cavity.

5. The intramedullary implant as recited in claim 4, wherein the fluted protruding member of the first piece and the fluted cavity of the second piece are complementarily tapered.

6. The intramedullary implant as recited in claim 5, wherein the first ends of the first and second pieces are fluted.

7. The intramedullary implant as recited in claim 5, further comprising a porous coating on a surface of the implant.

8. The intramedullary implant as recited in claim 7, wherein the porous coating comprises hydroxyapatite.

9. The intramedullary implant as recited in claim 7, wherein the porous coating comprises a roughness formed on the surface of the implant.

10. The intramedullary implant as recited in claim 7, wherein the porous coating comprises a biocompatible material partially embedded in the surface of the implant.

11. The intramedullary implant as recited in claim 10, wherein the biocompatible material is titanium.

12. The intramedullary implant as recited in claim 11, wherein the titanium comprises a coil.

13. The intramedullary implant as recited in claim 12, wherein the coil is embedded to a depth of between ⅓ to ½ of the diameter of the coil.

14. The intramedullary implant as recited in claim 13, wherein, prior to being embedded, the coil is wrapped around the implant.

15. The intramedullary implant as recited in claim 13, wherein, after the coil is embedded in the surface of the implant, the interstices between the nonembedded portions of the coil range from 150 to 200 micrometers.

16. The intramedullary implant as recited in claims 4, 7, 10, or 15, further comprising a thermoplastic polymer having an elastic modulus approximating the elastic modulus of bone.

17. The intramedullary implant as recited in claims 4, 7, 10 or 15 further comprising a fiber reinforced polymer, wherein the fiber reinforced polymer has an elastic modulus approximating the elastic modulus of bone.

18. The intramedullary implant as recited in claim 17, wherein the polymer comprises polyetheretherketone (PEEK).

19. The intramedullary implant as recited in claim 18, wherein the reinforcing fiber comprises glass.

20. The intramedullary implant as recited in claim 19, wherein the glass fibers comprise 10% of the implant by volume.

21. An orthopedic implant for replacing a missing or diseased portion of bone, the implant comprising a composite comprising:
   a thermoplastic polymer;
   a material for reinforcing the polymer;
   a biocompatible material partially embedded in a surface of the implant;
   a first piece and a second piece, the first and second pieces being joined and locked together by an interlocking means comprising:

a protruding member on the first piece; and a cavity in the second piece for receiving the protruding member; and means for resisting rotation between the first and second pieces, wherein the rotation resisting means comprises a flute on the protruding member and a corresponding fluted opening in the cavity;

wherein the composite has an elastic modulus approximating the elastic modulus of bone.

22. An orthopedic implant for replacing a missing or diseased portion of bone, the implant comprising a composite comprising:

polyetheretherketone (PEEK);

glass fibers for reinforcing the polymer, the glass fibers comprising 10% of the implant by volume;

a biocompatible material partially embedded in a surface of the implant;

a first piece and a second piece, the first and second pieces being joined and locked together by an interlocking means comprising:

a protruding member on the first piece; and a cavity in the second piece for receiving the protruding member; and means for resisting rotation between the first and second pieces, wherein the rotation resisting means comprises a flute on the protruding member and a corresponding fluted opening in the cavity;

wherein the composite has an elastic modulus approximating the elastic modulus of bone.

23. An orthopedic implant for replacing a missing or diseased portion of bone, the implant comprising a composite comprising:

a thermoplastic polymer;

a material for reinforcing the polymer;

a biocompatible material partially embedded in a surface of the implant;

a first piece and a second piece, the first and second pieces being joined and locked together by an interlocking means comprising:

a protruding member on the first piece; and a cavity in the second piece for receiving the protruding member wherein the protruding member and the cavity are complementarily tapered; and means for resisting rotation between the first and second pieces;

wherein the composite has an elastic modulus approximating the elastic modulus of bone.

24. An orthopedic implant for replacing a missing or diseased portion of bone, the implant comprising a composite comprising:

polyetheretherketone (PEEK);

glass fibers for reinforcing the polymer, the glass fibers comprising 10% of the implant by volume; and a biocompatible material partially embedded in a surface of the implant;

a first piece and a second piece, the first and second pieces being joined and locked together by an interlocking means comprising:

a protruding member on the first piece; and a cavity in the second piece for receiving the protruding member, wherein the protruding member and the cavity are complementarily tapered; and means for resisting rotation between the first and second pieces;

wherein the composite has an elastic modulus approximating the elastic modulus of bone.

* * * * *